US012391635B2

United States Patent
Callant et al.

(10) Patent No.: US 12,391,635 B2
(45) Date of Patent: Aug. 19, 2025

(54) OXIDATION OF SANTALENE TO SANTALOL

(71) Applicant: ISOBIONICS B.V., Geleen (NL)

(72) Inventors: Dominique Callant, Geleen (NL); Paul Alsters, Geleen (NL); Karin Dautzenberg, Geleen (NL); Angela Gonzalez De Castro, Geleen (NL); Robert Trokowski, Geleen (NL)

(73) Assignee: ISOBIONICS B.V., Geleen (NL)

( * ) Notice: Subject to any disclaimer, the term of this patent is extended or adjusted under 35 U.S.C. 154(b) by 615 days.

(21) Appl. No.: 17/764,559

(22) PCT Filed: Sep. 25, 2020

(86) PCT No.: PCT/EP2020/076917
§ 371 (c)(1),
(2) Date: Mar. 29, 2022

(87) PCT Pub. No.: WO2021/063831
PCT Pub. Date: Apr. 8, 2021

(65) Prior Publication Data
US 2022/0371976 A1 Nov. 24, 2022

(30) Foreign Application Priority Data

Oct. 2, 2019 (NL) ..................... 2023931

(51) Int. Cl.
*C07C 29/09* (2006.01)
*C07C 17/10* (2006.01)
*C07C 22/02* (2006.01)
*C07C 67/11* (2006.01)

(52) U.S. Cl.
CPC ............ *C07C 29/095* (2013.01); *C07C 17/10* (2013.01); *C07C 22/02* (2013.01); *C07C 67/11* (2013.01); *C07C 2601/16* (2017.05); *C07C 2602/42* (2017.05); *C07C 2603/64* (2017.05); *C07C 2603/66* (2017.05)

(58) Field of Classification Search
None
See application file for complete search history.

(56) References Cited

U.S. PATENT DOCUMENTS

| 3,281,432 A * | 10/1966 | Blumenthal ........... C11B 9/0076 |
| | | 549/457 |
| 4,510,319 A | 4/1985 | Willis et al. |
| 6,034,268 A | 3/2000 | Surburg et al. |
| 6,406,706 B1 | 6/2002 | Haque et al. |

FOREIGN PATENT DOCUMENTS

| JP | 56-075443 A | 6/1981 |
| JP | 2013-521299 A | 6/2013 |
| JP | 2017-536381 A | 12/2017 |
| WO | 2011/109411 A2 | 9/2011 |
| WO | 2016/087179 A1 | 6/2016 |
| WO | 2018/160066 A1 | 9/2018 |

OTHER PUBLICATIONS

International Search Report and Written Opinion received for PCT Patent Application No. PCT/EP2020/076917, mailed on Dec. 8, 2020, 10 pages.
Christenson et al., "Identification of TRANS-P-SANTALOL and EPZ-CIS+SANTALOL in East Indian Sandalwood Oil", Phytochemistry, 1981, pp. 1139-1141.
Nussbaumer et al., "(±)-1-[(1R*,2R*,8aS*)-1,2,3,5,6,7,8,8a-Octahydro-1,2,8,8-tetramethylnaphthalen-2-yl]ethan-1-one: Isolation and Stereoselective Synthesis of a Powerful Minor Constituent of the Perfumery Synthetic Iso E Super", Helvetica, vol. 82, Issue 7, 1999, pp. 1016-1024.

* cited by examiner

*Primary Examiner* — Ana Z Muresan
(74) *Attorney, Agent, or Firm* — Faegre Drinker Biddle & Reath LLP

(57) ABSTRACT

The invention relates to a process for the oxidation of santalene to santalol. The starting material is in particular a mixture comprising alpha-santalene, beta-santalene, epi-beta-santalene, trans-alpha-bergamotene and beta-bisabolene. The oxidation of the santalenes occurs via an intermediate chloro-santalene compound. Substitution of the chloro-substituent by acetate yielded the mixture of the corresponding santalyl acetates, which were hydrolyzed to yield the corresponding mixture of santalols.

12 Claims, No Drawings

OXIDATION OF SANTALENE TO SANTALOL

CROSS-REFERENCE TO RELATED APPLICATIONS

This application is a national stage application (under 35 U.S.C. § 371) of PCT/EP2020/076917, filed Sep. 25, 2020, which claims benefit of Netherlands Application No. 2023931, filed Oct. 2, 2019, both of which are incorporated herein by reference in their entirety.

The invention relates to a process for the oxidation of santalene to santalol. Sandalwood oil is a highly valued naturally occurring fragrance, which constitutes an important ingredient in perfumes, cosmetics, toiletries, aromatherapy and pharmaceuticals. It has a soft, sweet-woody and balsamic odor that is predominantly imparted from the sesquiterpene alcohols alpha-santalol and beta-santalol. The source of true sandalwood oil is *Santalum album*, an over-harvested, slow-growing protected tree, for which the demand cannot be met.

To relieve the pressure on natural sources of sandalwood oil, a number of biochemical production processes to obtain sandalwood or their precursors have been developed, in particular by applying genetically modified micro-organisms. For example, the precursor santalene has now become readily accessible on an industrial scale due to genetically engineered micro-organisms that have an improved expression of genes encoding for santalene synthase (WO2018/160066). Moreover, this santalene synthase produces a spectrum of santalene sesquiterpenes (comprising most notably beta-santalene, alpha-santalene, epi-beta-santalene, trans-alpha-bergamotene and beta-bisabolene) that reflects the composition of the corresponding santalols in the sandalwood oil. Accordingly, an efficient and scalable oxidation of santalene to santalol would open the way to the production of an attractive substitute for true natural sandalwood oil on an industrial scale.

In U.S. Pat. No. 4,510,319, a santalene oxidation method is described ("Willis method") wherein santalene is first reacted with calcium hypochlorite in the presence of dry ice (solid $CO_2$) to form the intermediate compound chloro-santalene, an allylic halide. Then, this intermediate is reacted with potassium acetate to form the corresponding santalyl acetate ester. Final hydrolysis of this ester then yields the desired santalol.

The problem with this method is however that it is difficult to scale up. For example, the method exhibits a variation in the selectivity of the chlorination reaction. This variation becomes more pronounced with an increasing scale of the reaction, leading to unacceptable proportions of the different sesquiterpenoids in the product. Also, the addition of the solid $CO_2$ to the reaction mixture initiates a highly exothermic reaction, which does not allow a safe upscaling of this reaction.

Another problem associated with the Willis method is that solids are present in the reaction mixture at multiple stages of the oxidation process, such as the calcium hypochlorite that is used in the first step and the calcium chloride that is generated during the ester formation. These solids hinder the stirring of the mixtures and slow down the reactions. This severely complicates the scale up of the reaction. Moreover, the disposal of stoichiometric amounts solid salts such as the calcium chloride is undesired from an environmental point of view.

Nussbaumer and co-workers disclosed for a perfume ingredient found in the synthetic Iso E Super® a stereoselective synthesis starting from alpha-ionone; a diastereoselective conjugate addition of Me2CuLi to alpha-ionone was followed by a haloform reaction, esterification, and isomerization of the single C=C bond by treatment with NaOCl and resulting allyl chloride was ozonized and transformed into the trimethyl(vinyl)octahydrocoumarin which was submitted to other modifications. However, this process is for a different substance and also is problematic in the industrial scale application and for other target molecules, for example due to the risk of accumulation of explosive $Cl_2O$ and/or toxic $Cl_2$ that may locally be formed when the acid is added to the bleach containing mixture, and the lack of specificity in case more than one double bond would available for chlorination.

It is therefore an objective of the invention to provide a novel process for the oxidation of santalene to santalol that reduces the risk of the accumulation of explosive intermediates like $Cl_2O$ or toxic substances like $Cl_2$ and further allows a safe scale up to industrial scale (e.g. process batches yielding more than 100 kg of santalol) while providing good selectivity for the desired product. It is also an objective that chemical wastes in such processes are minimized. It is a further objective of the invention to provide a process which produces the different santalol sesquiterpenoids in proportions that are closer to those of the natural sandalwood oil than when conventional synthetic methods, in particular traditional oxidation methods, are used.

It has now been found that one or more of these objectives can be met by the application of a particular oxidizing agent in combination with particular reagents and additives.

Accordingly, the present invention relates to a process for the synthesis of a compound of Formula (I)

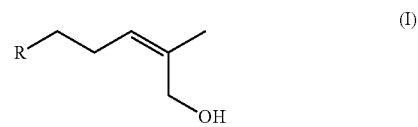

wherein R=a, b, c, d or e;

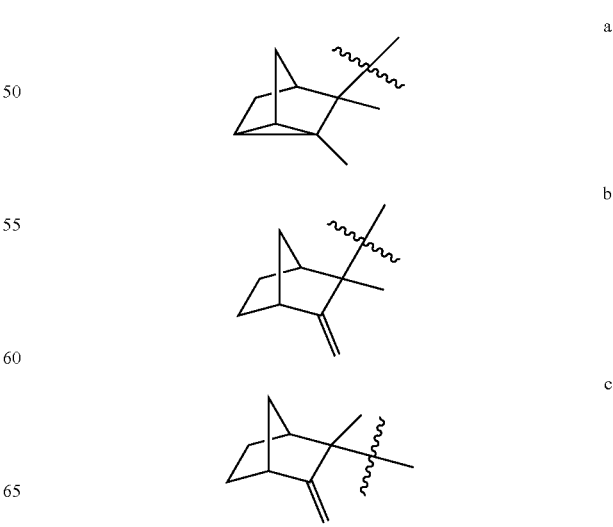

-continued

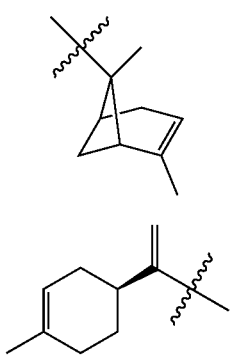
d

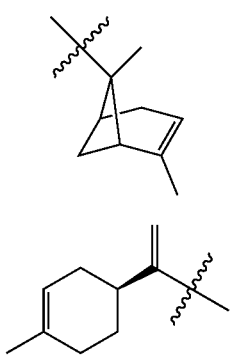
e comprising
the chlorination of a starting compound of Formula (II)

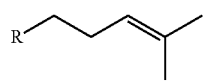
(II)

to an intermediate of Formula (III)

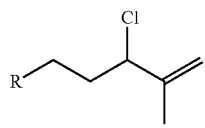
(III)

the conversion of the intermediate of Formula (III) to the compound of Formula (I);
wherein the chlorination comprises combining the starting compound of Formula (II) with an acid and an aqueous NaOCl solution.

Preferably, the chlorination step comprises providing a mixture of starting compound of Formula (II), optionally in the presence of a solvent for example but not limited to toluene, with all or at least part of the acid, followed by the subsequent step of contacting the mixture with all or a part of the aqueous NaOCl solution. When only a part of the needed amount of aqueous NaOCl solution is used to contact the mixture initially, the step of contacting the mixture with aqueous NaOCl solution is repeated as needed until the conversion of starting compound of Formula (II) to the intermediate of Formula (III) to the desired extent is achieved. In one embodiment, the step of contacting the mixture with aqueous NaOCl solution is performed in a stepwise manner or continuously at slow speed. During or after each contacting the mixture with aqueous NaOCl solution mixing is preferably used. The step of contacting the mixture with aqueous NaOCl solution may optionally include the simultaneous addition of a partial amount of the acid.

In one embodiment chlorination comprises combining the starting compound of Formula (II) with an acid and an aqueous NaOCl solution by providing the starting compound of Formula (II), optionally in the presence of a solvent for example but not limited to toluene, followed by the simultaneous addition of aqueous NaOCl solution and acid, preferably while mixing.

In one embodiment, the acid used in the methods of the invention can be a mixture of two or more acids, preferably a mixture of mild acids. In a further embodiment, the starting mixture of starting compound of Formula (II) comprises one or more types of acid, and during the contacting of the mixture with the aqueous NaOCl solution simultaneously acid of the same or different type(s) are added.

In one embodiment, the pH value of the mixture comprising the starting compound of Formula (II) is stable or increasing during the reaction, and preferably is increased at the end of the conversion of the intermediate of Formula (III) to the compound of Formula (I) compared to the start of the chlorination step.

The starting material for the process of the invention comprises one or more santalene sesquiterpenes of Formula (II) selected from the group of alpha-santalene (IIa), beta-santalene (IIb), epi-beta-santalene (IIc), trans-alpha-bergamotene (IId) and beta-bisabolene (IIe). Possibly, other santalene sequiterpenes are also present in the starting material.

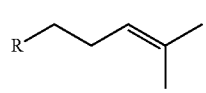
(II)

wherein R=a, b, c, d or e

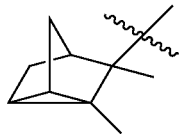
a

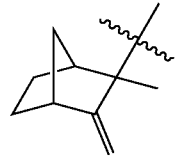
b

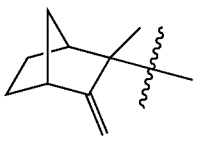
c

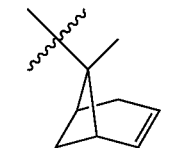
d

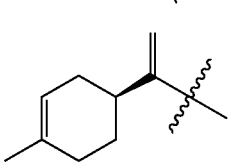
e

Then, the product of the process comprises one or more of the corresponding santalol sesquiterpenoids of Formula (I), i.e. alpha-santalol (Ia), beta-santalol (Ib), epi-beta-santalol (Ic), transalpha-bergamotol (Id) and Ianceol (Ie), respectively.

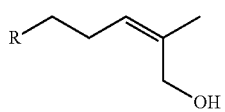
(I)

wherein R=a, b, c, d or e

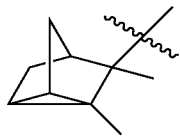 a

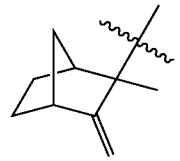 b

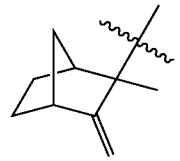 c

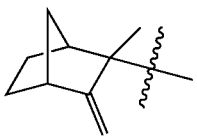 d

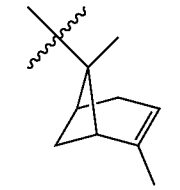 e wherein R=a, b, c, d or e

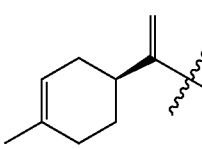 a

 b c d e

In this description, by the term "santalene sesquiterpene" is meant a compound of Formula (II) and by the term "santalol sesquiterpenoid" a compound of Formula (I). It is possible that other isomers of santalol sesquiterpenoids that occur in natural sandalwood oil in minor amounts are also produced by the process of the invention when the corresponding santalene sesquiterpene precursors are used as a starting material in the process. For example, cis-alpha-bergamotol and trans-beta-bergamotol may be formed in minor amounts from cis-alpha-bergamotene and trans-beta-bergamotene, respectively.

The conversion of santalene sesquiterpene (II) to santalol sesquiterpenoid (I) occurs via an intermediate that is the chlorinated santalene of Formula (III).

Further, in this description, by the term "chloro-santalene" is meant a compound of Formula (III), i.e. a santalene sesquiterpene that has undergone a chloro-substitution on its tail (i.e. on the terminal isoprene fragment).

The conversion of the chloro-santalene (III) to the intended santalol sesquiterpenoid product (I) is an allylic rearrangement that is believed to occur via an $S_N2'$ reaction mechanism. It is preferably performed by reaction with a carboxylate R'—COO yielding the intermediate santalyl acetate of Formula (IV), followed by its hydrolysis to yield the intended santalol sesquiterpenoid product (I).

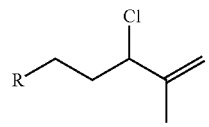
(III)

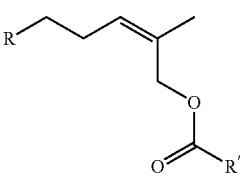
(IV)

wherein R=a, b, c, d or e;

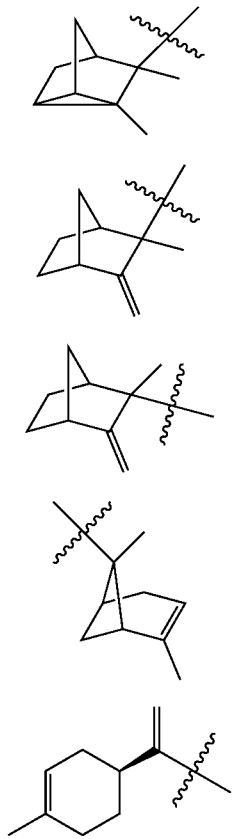

and wherein R' comprises an alkyl group of 1-7 carbon atoms.

The process of the invention may be carried out on only one of the santalene sesquiterpenes (II) or on any mixture thereof, because it is anticipated that the required reactivity at the tail is similar for the different santalene sesquiterpenes. In view of the aim to produce a close mimic of sandalwood oil (which is a mixture comprising at least the five santalol sesquiterpenoids (Ia-Ie) as mentioned above), the starting material usually comprises a mixture of the five santalene sesquiterpenes (IIa-IIe) as mentioned above, possibly supplemented with e.g. the minor components cis-alpha-bergamotene and trans-beta-bergamotene.

In particular, when the santalene sesquiterpene starting material was obtained by the microbiological methods as described in WO2018/160066, the most relevant santalene sesquiterpenes present are alpha-santalene (IIa; ~40 wt. %), beta-santalene (IIb; ~20 wt. %), epi-beta-santalene (IIc; ~2 wt. %), trans-alpha-bergamotene (IId; ~20% wt. %) and beta-bisabolene (IIe; ~3 wt. %). Subjecting this mixture to the process of the invention yields the corresponding santalol sesquiterpenoids in similar proportions. Possible deviations are e.g. due to over-chlorination of certain santalene sesquiterpenes (II) in the mixture (vide infra), because the over-chlorinated products usually cannot be converted into the corresponding santalol sesquiterpenoid. A perfumer evaluating the product obtained with a process of the invention on its similarity to natural sandalwood oil indicated that the perceived odor was "very good".

A first attempt to circumvent the use and production of solids in the process (as is the case in the Willis procedure) was the substitution of $Ca(ClO)_2$ with a solution of NaOCl in water (i.e. bleach). Although this initially gave promising results with respect to the yield and selectivity of the reaction, an undesired variation in the selectivity of the reaction was observed when the reaction was a performed multiple times, especially when a scale up of the reaction was attempted. This was ascribed to pH-variations caused by the addition of the solid $CO_2$.

It was then tried to perform the reaction under buffered conditions in the absence of dry-ice. Different buffers were therefore tested in a pH range of 4-10, but all of these resulted in barely any conversion of the santalene sesquiterpene starting material. More acidic environments were initially avoided in view of the risk of formation of $Cl_2O$, which is a highly reactive and explosive gas that is especially unwanted when the reaction is performed on a large scale. Accumulation of such species in the reaction mixture is hazardous in view of the risk on an explosion.

When the reaction was performed under more acidic conditions, the yields were also very low (only a few percent conversion to the desired santalol sequiterpenoids). Surprisingly, however, when a small excess of an acid was used in the reaction (with respect to the NaOCl), the chloro-santalenes were obtained in a yield and selectivity that are at least as high as those reported for the Willis procedure. Moreover, no variations in the selectivity of the reaction were observed when different runs were performed on a large scale (e.g. 10 kg of santalene), as was the case with dry-ice. The excess of acid is usually not more than five acid equivalents relative to the NaOCl. Typically, the excess is in the range of 1.05-3.0 acid equivalents relative to the NaOCl. Preferably, it is in the range of 1.1-2.0 acid equivalents, more preferably in the range of 1.2-1.6 acid equivalents. It may also be in the range of 1.2-2.5 acid equivalents, in the range of 1.4-2.2 acid equivalents or in the range of 1.6-1.9 acid equivalents. It may also be in the range of 1.05-1.8 acid equivalents, in the range of 1.1-1.6 acid equivalents, in the range of 1.15-1.5 acid equivalents, or in the range of 1.2-1.4 acid equivalents. In the chlorination, the NaOCl is usually present as an aqueous solution of 5-50 wt. % of NaOCl.

Usually, the NaOCl is present in excess to the santalene. For example, the molar excess of NaOCl relative to santalene is usually in the range of 1.0-2.0, in particular is it in the range of 1.1-1.9, more in particular it is in the range of 1.2-1.8 and even more in particular it is in the range of 1.3-1.7. It may also be in the range of 1.1-1.7, in the range of 1.2-1.5 or in the range of 1.25-1.45.

In particular, the acid is present in the range of 1.2-1.5 molar equivalents relative to the NaOCl, while the NaOCl is present in the range of 1.25-1.75 molar equivalents relative to santalene sesquiterpene. More in particular, the acid is present in the range of 1.25-1.45 molar equivalents relative to the NaOCl while the NaOCl is present in the range of 1.3-1.7 molar equivalents relative to santalene sesquiterpene.

In the procedure, the acid is usually first mixed with the santalene sesquiterpene, optionally in the presence of a solvent such as toluene. Then, the chlorination is performed by adding NaOCl as an aqueous solution in water (e.g. a 10-20 wt. % solution) very slowly to the santalene mixture. It is also possible to dose the acid simultaneously with the bleach, which is typically performed at relative speeds that correspond to the relative amounts that are overall added, so that the reaction mixture stays acidic during the reaction. The simultaneous dosing has the advantage that the pH of the reaction mixture is less subject to change during the reaction, in particular the initial pH is not as low as in the case where all the acid is present in the reaction mixture prior to the addition of the bleach.

Another advantage of this method is that the conversion and selectivity are almost independent of the dosage protocol, which allows a slow dosing of the NaOCl solution in the reactor. This minimizes the risks associated with having a large batch of such oxidizing material in the reaction mixture. Moreover, when the conversion of santalene sesquiterpene was followed during addition of the NaOCl solution, it appeared that chlorination of santalene sesquiterpene on the addition of NaOCl is almost instantaneous. Thus, there is a low risk of accumulation of the explosive $Cl_2O$. This opens the way to a safe scale up of the conversion to the intermediate chloro-santalene (III).

The acid may in principle be any acid that is compatible with the reaction conditions. It may be an inorganic acid, for example an acid selected from the group of sulfuric acid, hydrochloric acid and boric acid. Preferably, the acid is an acid with a pKa above 0, more preferably a mild acid with a pKa equal to or above 3.0. In a preferred embodiment the acid is a carboxylic acid. Generally, it is most effective that the applied acid dissolves in water under the reaction conditions applied and/or that it has a pKa value of 5.0 or less In case the acid is not dissolved during the reaction, it is preferred that the acid is a liquid during the reaction.

When a carboxylic acid is used, it is preferably selected from the group of formic acid, acetic acid, chloroacetic acid, dichloroacetic acid, trichloroacetic acid, propionic acid, 2-chloropropionic acid, 3-chloropropionic acid, trifluoroacetic acid, butyric acid, valeric acid, caproic acid, heptanoic acid, caprylic acid and benzoic acid. In one embodiment, a mild carboxylic acid with a pKa equal to or above 3 is used in the methods of the invention.

More preferably, the acid is acetic acid or formic acid or mixtures thereof, more preferably acetic acid. It was seen that the reactions run in the presence of acetic acid provided very good conversion and good selectivity towards the desired mono-chlorinated products. Moreover, the reaction showed excellent reproducibility.

The chlorination reaction is preferably carried out in a biphasic system, having an aqueous phase comprising the NaOCl and an organic phase comprising the santalene sesquiterpene starting material (II) and the chloro-santalene (III). The solvent of the organic phase preferably comprises toluene, or consists of toluene. Other solvents that may be applied are hydrocarbons such as a solvent selected from the group of heptane, hexane, cyclohexane, methylcyclohexane, decane and dodecane. Also halogenated hydrocarbons may be used, e.g. dichloromethane. It appeared however that the chlorination reaction is much cleaner in toluene than in e.g. dichloromethane, in that there are less chlorinated by-products. Further, it was found that particularly good yields were obtained when methylcyclohexane was used as a solvent.

Yet another solvent that may be used is diethyl ether. Further, it is also possible that the reaction is carried out neat, i.e. without a solvent.

The protocol using aqueous NaOCl under the acidic conditions in combination with an organic phase is also particularly convenient for a scale up protocol since 1) all the reagents are liquid; 2) no solids are generated during the process; and 3) the mechanical stirring is very efficient in the biphasic system that forms upon the addition of the bleach (water phase and organic phase).

It appeared difficult to convert the chloro-santalene (III) directly into the intended santalol sesquiterpenoid product (I), but a two stage process via an ester intermediate proved successful. Therefore, the conversion is preferably performed by reacting the chloro-santalene (III) with a carboxylate R'—COO⁻ to form the corresponding carboxylate ester of Formula (IV), wherein R' comprises an alkyl group of 1-7 carbon atoms;

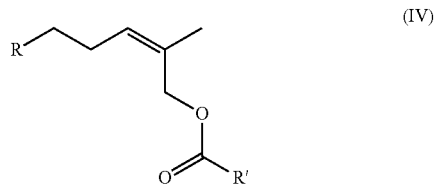

hydrolyzing the ester of Formula (IV) to the corresponding compound of Formula (I).

In this process, which entails a substitution reaction, the carboxylate is typically an alkyl carboxylate, e.g. with an alkyl chain of 1-8 carbon atoms, wherein such chain may comprise branches. In case of a branched chain, the total number of carbon atoms in the carboxylate is preferably in the range of 3-10. Preferably, the carboxylate is a C1-C5 carboxylate such as formate, acetate, propionate, butyrate and valerate. More preferably, the carboxylate is acetate and/or formate.

When formate is used as the carboxylate in the method of the invention, the reaction time is improved further and the isomer ratio of Z to E santalol increases further as well.

In another embodiment Potassium and/or Sodium salts of the acids are used, preferably Potassium acetate and/or Potassium formate.

The carboxylate may also be selected from the group of formate, benzoate and pivalate. The carboxylate is added prior to or during reaction, usually as a metal carboxylate, e.g. of sodium or potassium (R'—COONa or R'—COOK).

In one embodiment, instead of one carboxylate a mixture of carboxylates is used.

The hydrolysis of the carboxylate ester of Formula (IV) to the santalol (I) may be performed according to standard ester hydrolysis procedures known in the art. For example, it may be performed in methanol using potassium hydroxide as a base.

The present invention hence relates to a process for the synthesis of a compound of Formula (I)

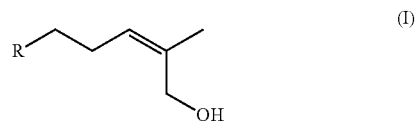

wherein R=a, b, c, d or e;

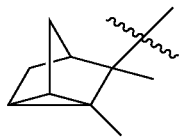

a b

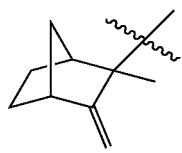

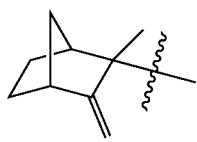

d

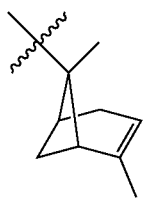

e

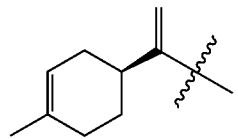

comprising the steps of:

providing a mixture of starting compound of Formula (II)

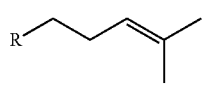
(II)

with an acid or a mixture of acids, optionally in the presence of a solvent for example but not limited to toluene;

and contacting the mixture with an aqueous NaOCl solution to produce an intermediate of Formula (III)

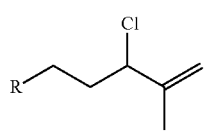
(III)

and reacting intermediate of Formula (III) with one or more carboxylate R'—COO to form the corresponding carboxylate ester(s) of Formula (IV), wherein R' comprises an alkyl group of 1-7 carbon atoms;

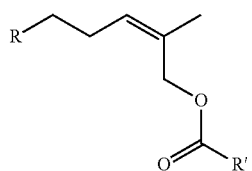
(IV)

and hydrolyzing the ester(s) of Formula (IV) to the corresponding compound of Formula (I).

The double bond in the allylic alcohol moiety of a compound of Formula (I) is in the Z-conformation when it concerns the natural sandalwood oil (no compounds with the E-conformation are observed therein). This is different when the santalol compound(s) is/are obtained via a process of the invention, because this process generates minor amounts of the E-isomer, for example in the range of 25-45 mol % (depending on the reaction conditions). Fortunately, the influence of this isomer on the organoleptic properties appeared to be minimal.

It appeared that the type of carboxylate and the organic solvent had a significant influence on the Z/E ratio of the formed santalol. The most favorable ratios were produced when the substitution reaction was performed in gamma-valerolactone with acetate or formate as the carboxylate. After conversion of the intermediate santalyl carboxylate (IV) to the final santalol (I), it appeared that the alpha-santalol (Ia) was formed as two conformational-isomers (Z and E) in a 65:35 ratio when acetate or formate was used. In fact, it is assumed that the other chloro-santalenes (IIIb-IIIe) furnish the same Z/E ratios, as only the terminal isoprene fragment (a common motif in all the isomers) is involved in the substitution reaction.

One embodiment of the invention relates to method according to the invention that produces the compound of Formula (I) in at least 55% as Z isomer, preferably at least 57%, 59%, 61%, 63% or at least 65% of the santalol are produced as Z isomer. In one embodiment, the method of the invention produces the compound of Formula (I) such as santalol in isomers (Z and E) in a ratio of 55:45, preferably 60:40, more preferably 65:35 or higher.

As stated above, the process of the invention may be carried out on only one of the santalene sesquiterpenes (II) or on any mixture thereof, because it is anticipated that the required reactivity at the tail is similar for the different santalene sesquiterpenes. Thus, when the starting material comprises two or more santalene sesquiterpenes of Formula (II), a process of the invention produces two or more of the corresponding santalol sesquiterpenoids of Formula (I).

Accordingly, a process of the invention may be a process wherein
the chlorination is performed on a mixture of compounds of Formula (II) to yield a mixture of the corresponding intermediates of Formula (III); and
the mixture of intermediates of Formula (III) is converted to a mixture of the corresponding compounds of Formula (I).

In one embodiment, the conversion of santalene to santalol is above 65%, preferably at least 70%, more preferably at least 80% and even more preferably at least 90%.

In particular, the mixture of compounds of Formula (II) comprises the compounds of Formula (IIa), Formula (IIb), Formula (IIc), Formula (IId) and Formula (IIe).

It was surprisingly found that when more than one equivalent of NaOCl was used, an over-chlorination of the santalene starting material (II) took place, wherein there is a strong a preference for the over-chlorination of trans-alpha-bergamotene (IId) as compared to the other santalenes (IIa), (IIb), (IIc) and (IIe). By over-chlorination is meant that more than one chloro-substituent is introduced on the santalene sesquiterpene starting material (II), in particular two or three chlorosubstituents. Unexpectedly, the over-chlorination was selective towards the trans-alpha-bergamotene (IId). This means that when the chlorination is performed on a mixture of compounds of Formula (IIa), (IIb), (IIc), (IId) and (IIe), the amount of chloro-santalene of Formula (IIId) is disproportionately low as compared to the other chloro-santalenes (IIIa), (IIIb), (IIIc) and (IIIe). This also has implications for the final santalol sequiterpenoid product (I), since it will contain a significantly lower proportion of trans-alpha-bergamotol than when no over-chlorination was applied. Since this is an isomer that is not particularly desired in the santalol mixture, sometimes even undesired, the method of over-chlorination opens the way to produce sandalwood oil with a decreased proportion of trans-alpha-bergamotol.

To this end, the over-chlorinated trans-alpha-bergamotene (IId) has to be removed or degraded at some stage of the process towards the santalol isoprenoids. It was found that distillation of the raw mixture obtained after the hydrolysis of santalyl acetate of Formula (IV) yielded the final santalol sesquiterpenoids of Formula (I) without any measurable amounts of over-chlorinated products, neither of any derivatives (such as diols or triols) or degradation products thereof.

In one embodiment, the method of the invention hence is a method as described herein wherein at least 60%, preferably at least 70% and more preferably at least 80% of trans-alpha-bergamotene was converted to derivates and these unwanted bergamotene derivates are easily removable by distillation.

The excess of NaOCl that is required for the over-chlorination should be enough to over-chlorinate the trans-alpha-bergamotene (IId), but a larger excess is not preferred since this gives undesired over-chlorination and/or degradation of the desired chloro-santalenes (IIIa), (IIIb), (IIIc) and (IIIe). Therefore, when it is aimed to decrease the content of trans-alpha-bergamotene (IId) in the product mixture, the molar excess of NaOCl is usually in the range of 2.1-3.5 with respect to the amount of trans-alpha-bergamotene (IId), preferably in the range of 2.2-3.2.

The ratio may however also depend on the reaction conditions that are applied, because not all NaOCl may be consumed as an oxidizing agent. For example, a significant part of the NaOCl may be converted in $Cl_2$. Any amount of this gas that escapes from the reaction mixture should be compensated for by a higher amount of NaOCl that is to be used in the chlorination reaction. The skilled person knows how to arrive at an appropriate excess of NaOCl given certain reaction conditions, by routine experimentation and without exerting inventive effort.

Thus, a in process of the invention, the chlorination of the mixture may comprise
the conversion of the compounds of Formula (IIa), (IIb), (IIc) and (IIe) to the intermediates of Formula (IIIa), (IIIb), (IIIc) and (IIIe); and
the introduction of two or three chloro-substituents on the compound of Formula (IId) to yield a di-chlorinated and/or a tri-chlorinated analogue of the compound of Formula (IIId);
wherein the di-chlorinated and/or tri-chlorinated analogue is/are removed from the intermediates of Formula (IIIa), (IIIb), (IIIc) and (IIIe) prior to or during the conversion of these intermediates to the corresponding compounds of Formula (IVa), (IVb), (IVc) and (IVe) and/or during the conversion of the compounds of Formula (IVa), (IVb), (IVc) and (IVe) to the corresponding compounds of Formula (Ia), (Ib), (Ic) and (Ie).

The invention further relates to a compound of Formula (IIId), which is the chlorinated trans-alpha-bergamotene, which can be separated from the reaction mixture after the chlorination. As elaborated above, this compound is an intermediate in the production of trans-alpha-bergamotol (Id).

The invention further relates to a compound of Formula (III)

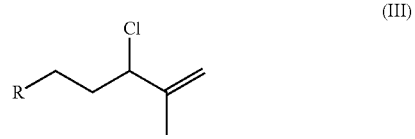

wherein R=a, b, c, d or e;

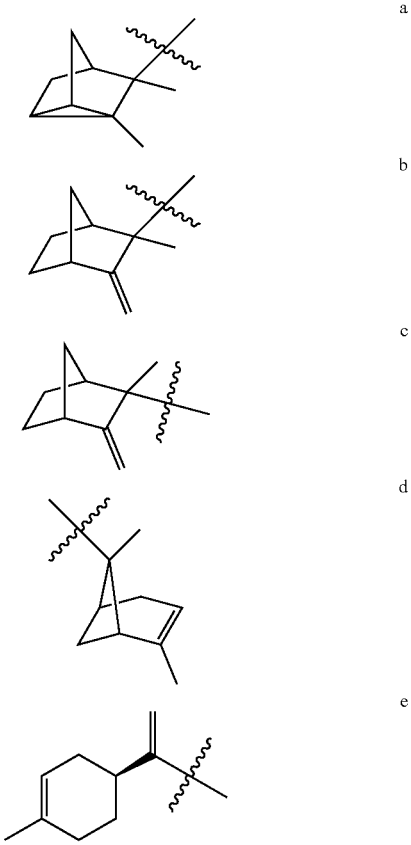

The invention further includes a composition obtainable by the methods of the invention comprising bergamotol, E santalol and Z santalol, wherein the amount of bergamotol, preferably trans-alpha-bergamotol, is not more than 15% (w/w), preferably not more than 12% (w/w) and more preferably not more than 10% (w/w) of the composition, and wherein Z santalol is in excess over E santalol. Preferably the Z santalol is in excess over E-Santalol in order of increasing preferences at least by 15% (w/w), 20% (w/w), 25% (w/w), 35% (w/w), 50% (w/w), 75% (w/w), 95% (w/w), 120% (w/w), 150% (w/w), 175% (w/w), 180% (w/w) or 185% (w/w). In another embodiment the ratio of Z to E santalol is at least 55:45, preferably 60:40 or higher, more preferably 65:35 or higher. Preferably the composition is a synthetic composition.

EXAMPLES

1. Chlorination of Santalene Sesquiterpenes (II)

In a 250 mL three-necked round bottom flask equipped with a magnetic stirrer, a thermometer and a dropping funnel, the santalene mix (10.0 g, obtained via the procedures as described in WO2018/160066), toluene (75 mL) and AcOH (6.0 mL) were added. NaOCl (14% $Cl_2$ solution) (33.75 and 34.50 mL) was put in the dropping funnel and added very slowly to the reaction mixture over a period of 2 h. An aliquot of the reaction was extracted and analyzed by GC. Afterwards, NaOCl (14% $Cl_2$ solution)(1 mL portions) was added in 30 min intervals until the starting santalene mixture (II) was fully converted to products. After completion of the reaction, $NaHCO_3$ solution was added to the reaction mixture and the organic phase was extracted. The organic phase was washed twice with NaCl solution, dried and the solvent evaporated in vacuo furnishing a yellow oil (11.98 g). The residue was analyzed by GC. About 80% of trans-alpha-bergamotene was converted to derivates and these unwanted bergamotene derivates are easily removable by distillation.

2. Substitution of the Chloro-Group of Chloro-Santalenes (III)

A 100 mL round bottom flask equipped with a magnetic stirrer was charged with the KOAc (7.46 g), KI (800 mg) and the chloro-santalene mix (5.0 g) obtained under Example 1 were added. DMA (30 mL) or Toluene/TBAB (30 mL/250 mg) were added as solvent. The reaction was placed in an oil bath and stirred at 110° C. in a 2 h reaction (DMA) or an overnight reaction (toluene/TBAB). The reaction progress was monitored by GC. After completion of the reaction, the reaction mixture was cooled down to room temperature and aqueous $NaHCO_3$ solution and n-pentane were added. The reaction mixture was transferred to a dropping funnel and the organic phase was extracted and washed with brine (or several times with LiCl solution in the case of DMA). The organic phase was dried over sodium sulfate, filtered and the solvent evacuated in vacuo to yield a light yellow oil. The residue was analyzed by GC and NMR.

3. Hydrolysis of the Santalyl Acetate Esters (IV)

A 100 mL round bottom flask equipped with a magnetic stirrer was charged with the santalyl acetates mixture (5.0 g) obtained under Example 2, KOH (5.0 g), $H_2O$ (6.8 mL) and MeOH (34 mL). The reaction mixture was heated to 60° C. for 10 min and stirred at room temperature for an additional 30 min. After completion of the reaction, water (ca. 60 mL) and n-pentane/Ac—OEt (4/1; 60/15 mL) were added to the reaction mixture. The organic phase was extracted and washed with brine. The organic phase was then dried over sodium sulfate and filtered. The solvent was removed in vacuo, furnishing a light yellow oil (4.0 g) which was analyzed by GC. The santalol sesquiterpenoids of Formula (I) were isolated as a mixture after distillation of this oil.

The conversion of santalene to santalol was above 90% and santalol was formed as two conformational-isomers (Z and E) in a 65:35 ratio. It was also found that trans-alpha-bergamotene resulted in trans-alpha-bergamotol present at much lower levels as the level of the initial trans-alpha-bergamotene and compared to levels when no over-chlorination was applied.

When in experiment 2 potassium formate replaced potassium acetate even better results were achieved.

LITERATURE CITED

Nussbaumer, C., Fráter, G. and Kraft, P. (1999), (±)-1-[(1R*,2R*,8aS*)-1,2,3,5,6,7,8,8a-Octahydro-1,2,8,8-tetramethylnaphthalen-2-yl]ethan-1-one: Isolation and Stereoselective Synthesis of a Powerful Minor Constituent of the Perfumery Synthetic Iso E Super®. HCA, 82: 1016-1024. doi:10.1002/(SIC1)1522-2675(19990707)82:7<1016:: AID-HLCA1016>3.0.CO;2-Y

The invention claimed is:

1. A process for the synthesis of a mixture of compounds of Formula (Ia), Formula (Ib), Formula (Ic), Formula (Id) and Formula (Ie),

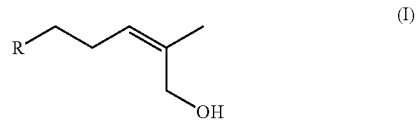

(I)

wherein R=a, b, c, d or e;

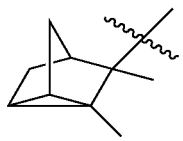

a

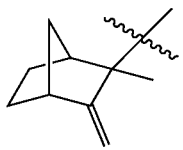

b

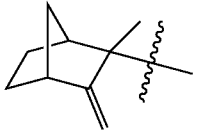

c

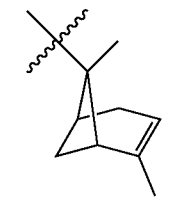

d

-continued

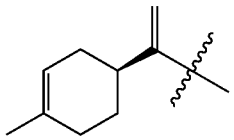
e and wherein Formula (Ia) corresponds to Formula (I) where R is a, Formula (Ib) corresponds to Formula (I) where R is b, Formula (Ic) corresponds to Formula (I) where R is c, Formula (Id) corresponds to Formula (I) where R is d, and Formula (Ie) corresponds to Formula (I) where R is e, the method comprising (1) chlorinating a mixture of compounds of Formula (II) by combining the starting compounds of Formula (II) with an acid and an aqueous NaOCl solution, wherein the mixture of compounds of Formula (II) comprises the compounds of Formula (IIa), Formula (IIb), Formula (IIc), Formula (IId) and Formula (IIe)

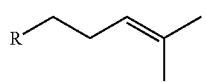
(II)

wherein Formula (IIa) corresponds to Formula (II) where R is a, Formula (IIb) corresponds to Formula (II) where R is b, Formula (IIc) corresponds to Formula (II) where R is c, Formula (IId) corresponds to Formula (II) where R is d, and Formula (IIe) corresponds to Formula (II) where R is e, to a mixture of intermediates of Formula (IIIa), Formula (IIIb), Formula (IIIc) and Formula (IIIe) and a di-chlorinated and/or a tri-chlorinated analogue of intermediate of Formula (IIId)

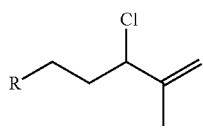
(III)

wherein Formula (IIIa) corresponds to Formula (III) where R is a, Formula (IIIb) corresponds to Formula (III) where R is b, Formula (IIIc) corresponds to Formula (III) where R is c, Formula (IIId) corresponds to Formula (III) where R is d, and Formula (IIIe) corresponds to Formula (III) where R is e, wherein the chlorinating step comprises
converting the starting compounds of Formula (IIa), Formula (IIb), Formula (IIc) and Formula (IIe) to the intermediates of Formula (IIIa), Formula (IIIb), Formula (IIIc) and Formula (IIIe); and
introducing two or three chloro-substituents on the starting compound of Formula (IId) to yield the di-chlorinated and/or tri-chlorinated analogue of the intermediate of Formula (IIId);

conversion of (2) converting a mixture of intermediates of Formula (IIIa), Formula (IIIb), Formula (IIIc) and Formula (IIIe) to a mixture of compounds of Formula (Ia), Formula (Ib), Formula (Ic) and Formula (Ie) by reacting the intermediate of Formula (III) with a carboxylate R'—COO⁻ to form the corresponding carboxylate ester of Formula (IV), wherein the carboxylate is selected from the group consisting of acetate, formate, propionate, butyrate, valerate, benzoate, pivalate, and mixtures thereof

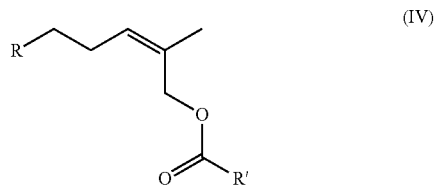
(IV)

and hydrolyzing the carboxylate ester of Formula (IV) to obtain the mixture of compounds of Formula (Ia), Formula (Ib), Formula (Ic) and Formula (Ie), wherein the di-chlorinated and/or tri-chlorinated analogue of the intermediate of Formula (IIId) is removed from the mixture prior to or during the conversion of intermediates of Formula (IIIa), Formula (IIIb), Formula (IIIc), and Formula (IIIe) to the mixture of compounds of Formula (Ia), Formula (Ib), Formula (Ie) and Formula (Ie).

2. The process according to claim 1, wherein the acid is a carboxylic acid.

3. The process according to claim 2, wherein the carboxylic acid is selected from the group of formic acid, acetic acid, chloroacetic acid, dichloroacetic acid, trichloroacetic acid, propionic acid, 2-chloropropionic acid, 3-chloropropionic acid, trifluoroacetic acid, butyric acid, valeric acid, caproic acid, heptanoic acid, caprylic acid and benzoic acid.

4. The process according to claim 1, wherein the acid is present in an amount in the range of 1.05-3.0 acid equivalents relative to the NaOCl.

5. The process according to claim 1, wherein the NaOCl is present in an amount in the range of 1.1-1.9 molar equivalents relative to the starting compound of Formula (II).

6. The process according to claim 1, wherein the acid is present in an amount in the range of 1.2-1.5 acid equivalents relative to the NaOCl while the NaOCl is present in an amount in the range of 1.25-1.75 molar equivalents relative to the starting compound of Formula (II).

7. The process according to claim 1, wherein the chlorinating step is performed in the presence of an organic solvent.

8. The process according to claim 1, wherein the carboxylate is acetate, formate or propionate.

9. The process according to claim 1, wherein the NaOCl is present in the chlorinating step in an amount in the range of 2.1-3.5 molar equivalents relative to the starting compound of Formula (IId).

10. The process according to claim 1, wherein the compound of Formula (I) is produced in isomers (Z and E) in a ratio of 55:45 or higher.

11. A compound of Formula (III)

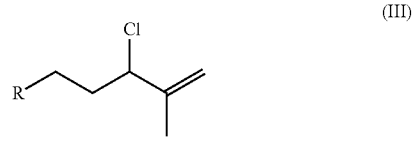
(III)

wherein R=e;
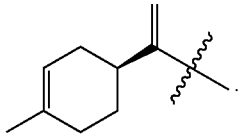 e
12. A mixture of compounds of Formula (III) comprising compound of Formula (IIIa), compound of Formula (IIIb), compound of Formula (IIIc) and compound of Formula (IIIe) and comprising a di-chlorinated and/or a tri-chlorinated analogue of the intermediate of Formula (IIId)
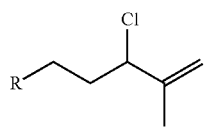 (III)
wherein R=a, b, c, d or e:
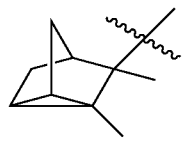 a
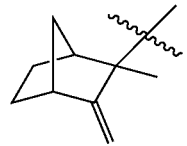 b
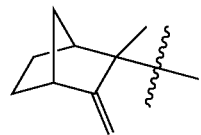 c
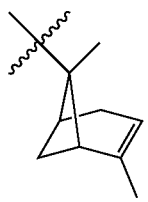 d
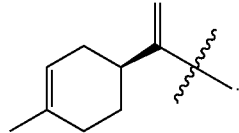 e
* * * * *